United States Patent
Chen (10) Patent No.: US 9,987,271 B2
(45) Date of Patent: *Jun. 5, 2018

(54) METHOD OF TREATING NASOPHARYNGEAL CARCINOMA USING PERILLYL ALCOHOL DERIVATIVE

(71) Applicant: NeOnc Technologies, Inc., West Hollywood, CA (US)

(72) Inventor: Thomas Chen, La Canada, CA (US)

(73) Assignee: NeOnc Technologies, Inc., Los Angeles, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/429,556

(22) Filed: Feb. 10, 2017

(65) Prior Publication Data

US 2017/0151233 A1    Jun. 1, 2017

Related U.S. Application Data

(63) Continuation of application No. 14/923,896, filed on Oct. 27, 2015, and a continuation-in-part of application No. 15/291,847, filed on Oct. 12, 2016, which is a continuation of application No. 13/818,972, filed as application No. PCT/US2011/049392 on Aug. 26, 2011, now Pat. No. 9,499,461.

(60) Provisional application No. 62/069,000, filed on Oct. 27, 2014, provisional application No. 61/377,747, filed on Aug. 27, 2010, provisional application No. 61/471,402, filed on Apr. 4, 2011.

(51) Int. Cl.
| | |
|---|---|
| A61K 31/495 | (2006.01) |
| A61K 45/06 | (2006.01) |
| A61K 9/00 | (2006.01) |
| A61M 15/00 | (2006.01) |
| A61M 15/08 | (2006.01) |
| A61K 47/54 | (2017.01) |

(52) U.S. Cl.
CPC .......... *A61K 31/495* (2013.01); *A61K 9/0019* (2013.01); *A61K 9/0043* (2013.01); *A61K 9/0073* (2013.01); *A61K 45/06* (2013.01); *A61K 47/542* (2017.08); *A61M 15/009* (2013.01); *A61M 15/08* (2013.01)

(58) Field of Classification Search
CPC ................................. A61K 9/00; A61K 45/06
See application file for complete search history.

(56) References Cited

FOREIGN PATENT DOCUMENTS

WO    WO 2012027693 A2 *  3/2012  ........... A61K 31/415

* cited by examiner

*Primary Examiner* — Samira Jean-Louis
(74) *Attorney, Agent, or Firm* — Leason Ellis LLP (57) ABSTRACT

A method of treating nasopharyngeal carcinoma in a mammal includes delivering to the mammal a therapeutically effective amount of a perillyl alcohol (POH) carbamate which is a perillyl alcohol conjugated with temozolomide (TMZ).

11 Claims, 9 Drawing Sheets
(5 of 9 Drawing Sheet(s) Filed in Color)

METHOD OF TREATING NASOPHARYNGEAL CARCINOMA USING PERILLYL ALCOHOL DERIVATIVE

CROSS REFERENCE TO RELATED APPLICATION

This application is a continuation of U.S. application Ser. No. 14/923,896 filed Oct. 27, 2015, which claims benefit of U.S. Provisional Application No. 62/069,000 filed Oct. 27, 2014. This application is also a continuation-in-part of U.S. application Ser. No. 15/291,847 filed Oct. 12, 2016, which is a continuation of U.S. application Ser. No. 13/838,972, which is the national stage of PCT/US11/49392, which claims priority to U.S. Provisional Application Nos. 61/471,402 and 61/377,747.

FIELD OF THE INVENTION

The present invention relates to methods of using perillyl alcohol derivative for treating nasopharyngeal carcinoma.

BACKGROUND OF THE INVENTION

Nasopharyngeal carcinoma (NPC) is a tumor arising from the epithelial cells of the nasopharynx, which is located behind the nose and above the back of the throat. NPC differs significantly from other cancers of the head and neck, based on its causes, occurrence, clinical behavior, and treatment options. It is uncommon in the United States, but occurs much more frequently in other parts of the world, especially in Southeast Asia, including the Guangdong province of southern China, and Taiwan.

NPC's difficult-to-observe location behind the nose, where the nasal passages and auditory tubes join the remainder of the upper respiratory tract, creates two major hurdles for effective therapy. First, due to its hidden location, NPC is usually diagnosed quite late during its development and in fact, the diagnosis is often made by lymph node biopsy, when the primary cancer already has begun to spread to other parts of the body. Second, the anatomical position of the primary tumor is not easily amenable for surgery and local control, which is why biopsies are performed on cervical lymph node metastases, rarely on the primary tumor.

Treatment of NPC usually involves radiation therapy, chemotherapy, or a combination of the two. Surgery, which is rarely used, may be applied to remove cancerous lymph nodes in the neck area. The exact treatment plan is devised based on several factors, including stage of the cancer, overall health of the patient, and the extent of side effects the patient is willing tolerate. However, despite initially successful treatment, many patients will relapse after treatment, and management of NPC remains one of the biggest clinical challenges. Overall survival after recurrence is quite poor with median survival ranging from 7 to 22 months. B. Brennan, Nasopharyngeal carcinoma, *Orphanet J Rare Dis* 1 (2006) 23; S. M. Cao, et al., The prevalence and prevention of nasopharyngeal carcinoma in China, *Chin J Cancer* 30 (2011) 114-119; W. I. Wei, et al. Nasopharyngeal carcinoma. Lancet 365 (2005) 2041-2054; J. Tsang et al., Novel therapy for nasopharyngeal carcinoma—where are we. *Oral Oncol* 50 (2014) 798-801; L. Jang-Chun et al., Comparisons of quality of life for patients with nasopharyngeal carcinoma after treatment with different RT technologies, *Acta Otorhinolaiyngol Ital* 34 (2014) 241-246. Therefore, more effective and better-tolerated treatment options for NPC are needed.

SUMMARY OF THE INVENTION

In one aspect, the present invention provides a method for treating nasopharyngeal carcinoma in a mammal, comprising the step of delivering to the mammal a therapeutically effective amount of a perillyl alcohol carbamate, wherein the perillyl alcohol carbamate comprises perillyl alcohol conjugated with temozolomide (TMZ). In one embodiment, the perillyl alcohol carbamate is 3-methyl 4-oxo-3,4-dihydroimidazo[5,1-d][1,2,3,5]tetrazine-8-carbonyl)-carbamic acid-4-isopropenyl cyclohex-1-enylmethyl ester.

The perillyl alcohol carbamate can be administered by inhalation, intranasally, orally, intravenously, subcutaneously or intramuscularly. In embodiment, the perillyl alcohol carbamate is administered intranasally using an atomizer, e.g., by a nasal delivery device. The nasal delivery device can be an intranasal inhaler, an intranasal spray device, an atomizer, a nebulizer, a metered dose inhaler (MDI), a pressurized dose inhaler, an insufflator, a unit dose container, a pump, a dropper, a nasal spray bottle, a squeeze bottle, or a bi-directional device In one embodiment, the method further comprises the step of treating the mammal with radiation. In another embodiment, the method further comprises the step of delivering to the mammal one or more chemotherapeutic agents. Chemotherapeutic agents are selected from, but not limited to, Rituximab, Beuacizumab, Trastuzumab, Imatinib, Lenalidomide, Pemetrexed, Bortezomib, Cetuximab, Leuprorelin, Abiraterone, 5-Fluorouracil, Doxorubicin, Epirubicin, Gemeitabine, Methotrexate, all trans Retinoic Acid, Azacitidine, Azathioprine, Bleomycin, Carboplatin, Capecitabine, Cisplatin, Chlorambucil, Cyclophosphoramide, Cytarabine, Daunorubicin, Docetaxel, Doxifluridine, Epothilone, Etoposide, Hydroxyurea, Idarubicin, Irinotecan, Mechlorethamine, Mercaptopurine, Methotrexate, Mitoxantrone, Oxaliplatin, Paclitaxel, Teniposide, Tioguanine, Topotecan, Valrubicin, Vincristine, Vinblastine, Vindesine and Vinorelbine.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The present invention provides for a method of treating nasopharyngeal carcinoma in a mammal, e.g., human, by administering to the mammal a therapeutically effective amount of perillyl alcohol (POH) carbamate that comprises POH conjugated with TMZ. The chemical formula of the compound is 3-methyl 4-oxo-3,4-dihydroimidazo[5,1-d][1,2,3,5]tetrazine-8-carbonyl)-carbamic acid-4-isopropenyl cyclohex-1-enylmethyl ester, which is herein also referred to as TMZ-POH (or POH-TMZ). The structure of TMZ-POH is as follows:

TMZ-POH may be formulated into a pharmaceutical composition, where TMZ-POH is present in amounts ranging from about 0.01% (w/w) to about 100% (w/w), from about 0.1% (w/w) to about 80% (w/w), from about 1% (w/w) to about 70% (w/w), from about 10% (w/w) to about 60% (w/w), or from about 0.1% (w/w) to about 20% (w/w). TMZ-POH can be administered alone, or may be co-administered together with radiation (including brachytherapy) or one or more other agents (e.g., a chemotherapeutic agent such as, but not limited to, Rituximab, Beuacizumab, Trastuzumab, Imatinib, Lenalidomide, Pemetrexed, Bortezomib, Cetuximab, Leuprorelin, Abiraterone, 5-Fluorouracil, Doxorubicin, Epirubicin, Gemeitabine, Methotrexate, all trans Retinoic Acid, Azacitidine, Azathioprine, Bleomycin, Carboplatin, Capecitabine, Cisplatin, Chlorambucil, Cyclophosphoramide, Cytarabine, Daunorubicin, Docetaxel, Doxifluridine, Epothilone, Etoposide, Hydroxyurea, Idarubicin, Irinotecan, Mechlorethamine, Mercaptopurine, Methotrexate, Mitoxantrone, Oxaliplatin, Paclitaxel, Teniposide, Tioguanine, Topotecan, Valrubicin, Vincristine, Vinblastine, Vindesine and Vinorelbine), to treat nasopharyngeal carcinoma. Treatments may be sequential, with the POH-TMZ being administered before or after the administration of other agents. Alternatively, agents may be administered concurrently. The route of administration may vary, and can include, inhalation, intranasal, oral, transdermal, intravenous, subcutaneous or intramuscular injection.

TMZ-POH may also be co-administered with antiviral agents, anti-inflammatory agents or antibiotics. The agents may be administered concurrently or sequentially. TMZ-POH can be administered before, during or after the administration of the other active agent(s).

TMZ-POH may be used in combination with radiation therapy. In one embodiment, the present invention provides for a method of treating nasopharyngeal carcinoma, with radiation, where the cells are treated with an effective amount of TMZ-POH, and then exposed to radiation. TMZ-POH treatment may be before, during and/or after radiation. For example, the TMZ-POH may be administered continuously beginning one week prior to the initiation of radiotherapy and continued for two weeks after the completion of radiotherapy.

TMZ-POH may be administered by any method known in the art, including, without limitation, intranasal, oral, transdermal, ocular, intraperitoneal, inhalation, intravenous, ICV, intracisternal injection or infusion, subcutaneous, implant, vaginal, sublingual, urethral (e.g., urethral suppository), subcutaneous, intramuscular, intravenous, rectal, sub-lingual, mucosal, ophthalmic, spinal, intrathecal, intra-articular, intra-arterial, sub-arachinoid, bronchial and lymphatic administration. The details of the administration and preparation of compositions for different administration routes are described in PCT application PCT/US2011/049392, published as WO 2012027693, the disclosure of which is incorporated by reference herein in its entirety.

As used herein, the term "therapeutically effective amount" is an amount sufficient to treat a specified disorder or disease or alternatively to obtain a pharmacological response treating a disorder or disease. Methods of determining the most effective means and dosage of administration can vary with the composition or compound used for therapy, the purpose of the therapy, the target cell being treated, and the subject being treated. Treatment dosages generally may be titrated to optimize safety and efficacy. Single or multiple administrations can be carried out with the dose level and pattern being selected by the treating physician. Suitable dosage formulations and methods of administering the agents can be readily determined by those of skill in the art. For example, the composition are administered at about 0.01 mg/kg to about 200 mg/kg, about 0.1 mg/kg to about 100 mg/kg, or about 0.5 mg/kg to about 50 mg/kg. When the compounds described herein are co-administered with another agent or therapy, the effective amount may be less than when the agent is used alone.

TMZ-POH can be synthesized by a process comprising reacting a first reactant of perillyl chloroformate with a second reactant temozolomide. The reaction may be carried out in the presence of tetrahydrofuran and a base such as n-butyl lithium. POH chloroformate may be made by reacting POH with phosgene. For example, POH conjugated with temozolomide through a carbamate bond may be synthesized by reacting temozolomide with oxalyl chloride followed by reaction with perillyl alcohol. The reaction may be carried out in the presence of 1,2-dichloroethane. The resulting compound is (3-methyl 4-oxo-3,4-dihydroimidazo[5,1-d][1,2,3,5]tetrazine-8-carbonyl)carbamic acid-4-isopropenyl cyclohex-1-enylmethyl ester. The details of the chemical reactions generating this compound are described in PCT application PCT/US2011/049392, published as WO 2012027693.

The following example illustrates some aspects of the present invention and is not to be construed as limiting. In the figures discussed in this example, TMZ-POH is also referred to as NEO212.

EXAMPLE 1

In Vitro Studies of TMZ-POH in NPC Cell Lines

Two representative NPC cell lines, TW1 and TW4, were used. TW1 and TW4 had previously been established from patients with cancer of the nasopharynx. C. T. Lin et al., Characterization of seven newly established nasopharyngeal carcinoma cell lines, *Lab Invest* 68 (1993) 716-727; C. D. Wu et al., Nucleolin antisense oligodeoxynucleotides induce apoptosis and may be used as a potential drug for nasopharyngeal carcinoma therapy, *Oncol Rep* 27 (2012) 94-100.

Figure 1:
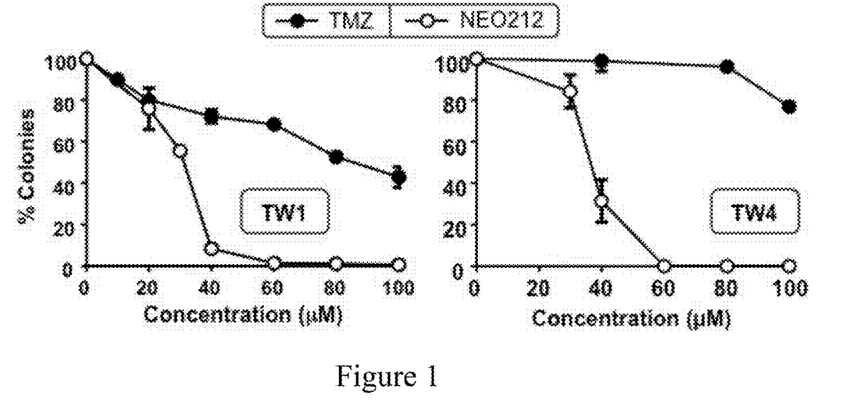
FIG. 1 shows survival and colony-formation of the TW1 and TW4 NPC cell lines which were treated with increasing concentrations of TMZ-POH or TMZ for 48 hours.

In a first experiment, TW1 and TW4 cell lines were kept in cell culture and treated with increasing concentrations of TMZ-POH or TMZ for 48 hours. Cellular survival and ability to continue to proliferate was determined thereafter. After 48 hours, the drugs were removed and the cells received fresh medium without any drugs added. The cells were left undisturbed for 12 days, after which time the number of newly formed colonies was determined. The number of colonies from those cultures that had not received any drugs, or had received vehicle only, was set at 100%. As shown in FIG. 1, TMZ-POH caused pronounced inhibition of cell growth, and this inhibitory or cytotoxic effect was much more potent than the effect of TMZ. TMZ-POH at a concentration of 60 $\mu$M completely prevented any and all colony formation (0% survival) in both cell lines. The IC50 (i.e., the concentration required to inhibit cell growth by 50%) of TMZ-POH was about 35 $\mu$M; in comparison, TMZ at a concentration of about 90 $\mu$M could only kill 50% of TW1 cells, and was unable to kill half of TW4 cells, even at 100 $\mu$M.

Figure 2:
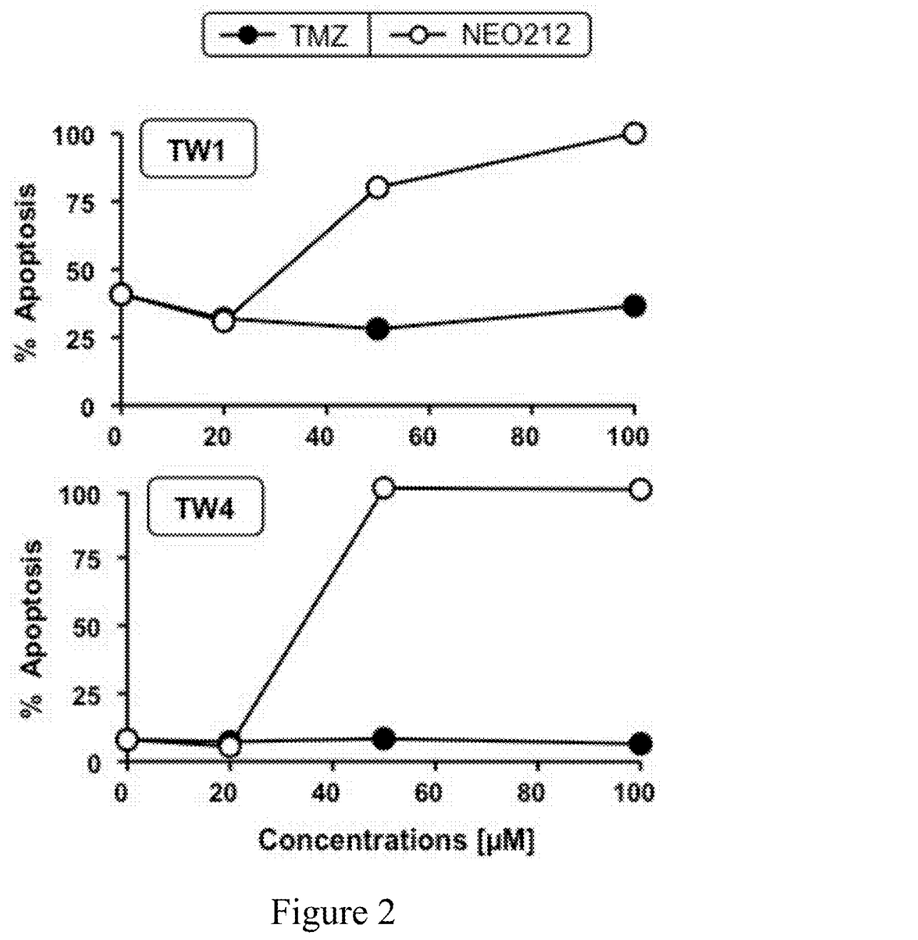
FIG. 2 shows quantitative evaluation of cytotoxicity and apoptosis in TW1 and TW4 NPC cell lines after TW1 and TW4 cells were treated with increasing concentrations of TMZ-POH or TMZ for 24 hours.

In another experiment, the extent of cell death (apoptosis) caused by treatment of NPC cell lines with TMZ-POH or with TMZ in vitro was quantified. The extent of cell death/apoptosis was measured with a cell death ELISA kit after TW1 and TW4 cells were treated with increasing concentrations of TMZ-POH or TMZ for 24 hours. As shown in FIG. 2, TMZ-POH caused much greater cytotoxicity than TMZ in both NPC cell lines, TW1 and TW4. In fact, up to 100 $\mu$M TMZ did not exert any cytotoxic effect, whereas the same concentration of TMZ-POH resulted in 100% cell killing. The effect was even more pronounced in the TW4 cell line, where 50 $\mu$M TMZ-POH was sufficient to cause 100% apoptosis, effectively killing the entire cell culture.

Figure 3:
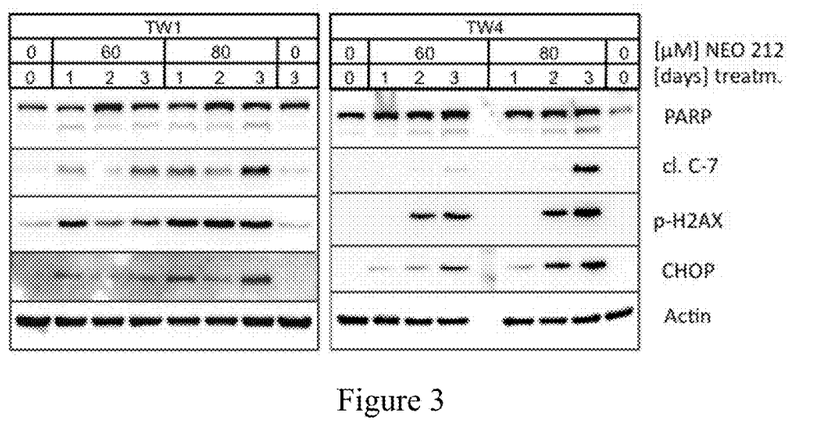
FIG. 3 shows induction of molecular indicators of cell stress, DNA damage, and cell deathlapoptosis in TW1 and TW4 cell lines after the TW1 and TW4 cells were treated with different concentrations of TMZ-POH for 1, 2, and 3 days.

Highly effective cancer cell killing by TMZ-POH, demonstrated above with two different cellular methods, was further confirmed at the molecular level. To this end, NPC cells were treated with 60 or 80 $\mu$M TMZ-POH for 1, 2, or 3 days, followed by the analysis of protein markers of cell death, DNA damage, and cellular stress. Cellular proteins were harvested and analyzed for PARP (poly ADP-ribose polymerase 1) cleavage (i.e., appearance of a faster migrating band) and cleaved caspase 7 (cl. C-7), both of which are markers or indicators of an ongoing cell death process. The DNA damage marker was p-H2AX (i.e., the phosphorylated form of histone 2A family member X protein). As a marker for cellular stress, CHOP (C/EBP homologous protein, also called GADD153) was used. As shown in FIG. 3, treatment of NPC cell lines with TMZ-POH resulted in pronounced elevation of all these markers, indicating effective induction of cellular stress (in particular endoplasmic reticulum stress), DNA damage, and apoptosis in response to treatment with TMZ-POH.

EXAMPLE 2

In Vivo Studies of TMZ-POH in NPC Animal Models

The potent anticancer effects of TMZ-POH were also verified in an animal (mouse) model of NPC. TW4 NPC cells were implanted into the flanks of 18 athymic nude mice (Harlan Laboratories, Indianapolis, Ind.). In order to be able to more precisely monitor and document tumor growth, these cells had been labeled with the firefly luciferase gene, which allows whole-body, non-invasive bioluminescent imaging of animals before, during, and after drug treatment to reveal tumor size in each animal. Once tumors had begun to grow in each animal, the animals were separated into three groups of 6 animals each. The first group of animals was the control group, without any drug treatment. In the second group, each animal received 5 mg/kg TMZ-POH once daily. In the third group, each animal received 30 mg/kg TMZ-POH once daily. The drug was administered by subcutaneous injection into the neck area. Daily injections were also performed for each animal in the first (control) group, but here the animals received vehicle only (containing glycerol and ethanol but without any active drug ingredient).

Figure 4:
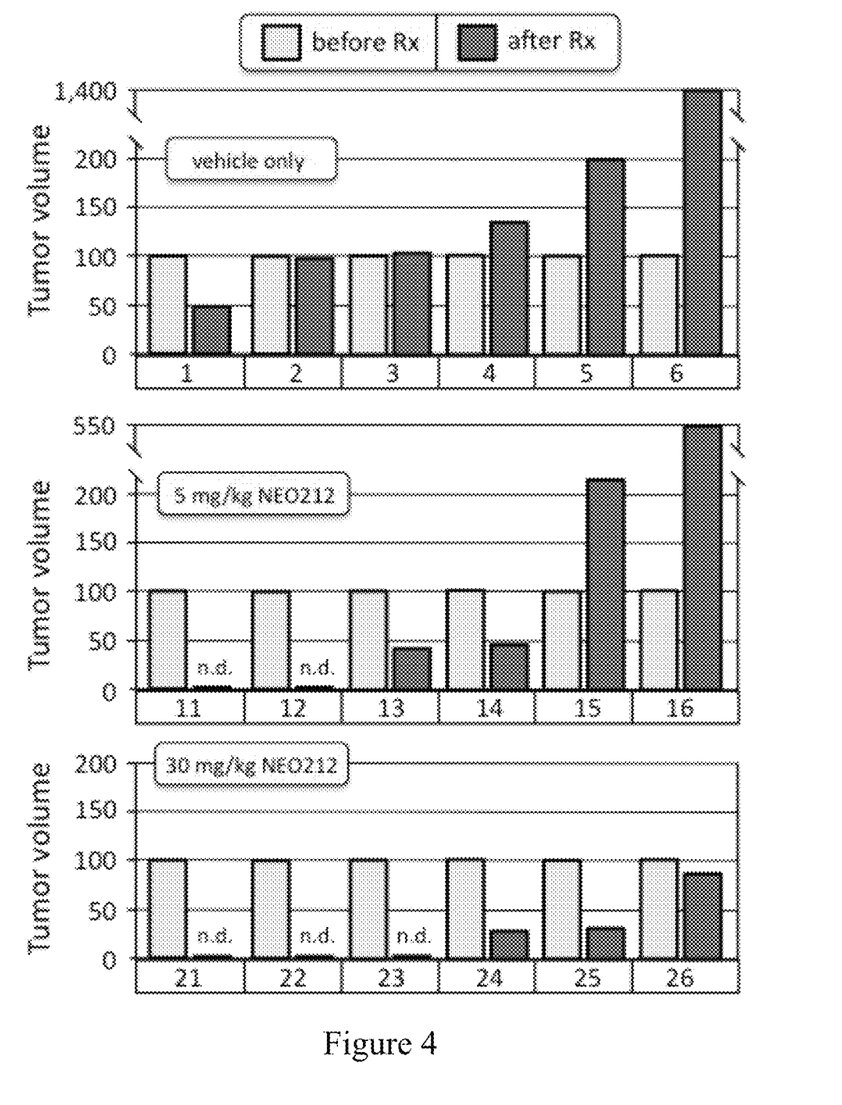
FIG. 4 shows tumor growth of 18 NPC mice that were treated with vehicles and different dosages of TMZ-POH.

FIG. 4 presents the tumor growth result of these animals, where animals #1-6 received vehicle only (no TMZ-POH), animals #11-16 received 5 mg/kg TMZ-POH, and animals #21-26 received 30 mg/kg TMZ-POH. All animals received once-daily injections for 28 days. Tumor volume was measured by bioluminescent imaging of all animals (see also FIG. 5) before the onset of treatment (light gray bars, before Rx) and again one day after the termination of the 28-day treatment regimen (dark gray bars, after Rx). The extent of bioluminescence (total light flux) for each animal was converted to 100% before drug treatment to facilitate comparison. (n.d.: not detectable.). As shown in FIG. 4, in the vehicle-only group, there was one animal where the tumor had regressed by 50% at the end of the 28-day period; two animals displayed unchanged tumor volume, and three animals displayed increased tumor growth, with one tumor reaching about 14 times initial volume. In comparison, there was no increase in tumor volume in those animals that received 30 mg/kg TMZ-POH (bottom chart). Here, three tumors disappeared (i.e., became undetectable, n.d.) after 28 days of drug treatment, and three tumors shrank. Animals treated with 5 mg/kg TMZ-POH also responded with reduced tumor growth, although not as pronounced as those animals that received the higher dosage. Although not shown, it is noted that drug-treated animals did not display discernable side effects of TMZ-POH treatment, indicating that TMZ-POH was well tolerated by these animals. This is a relevant because systemic toxicity and organ damage is undesirable during treatment with many established chemotherapeutic drugs.

Figure 5:
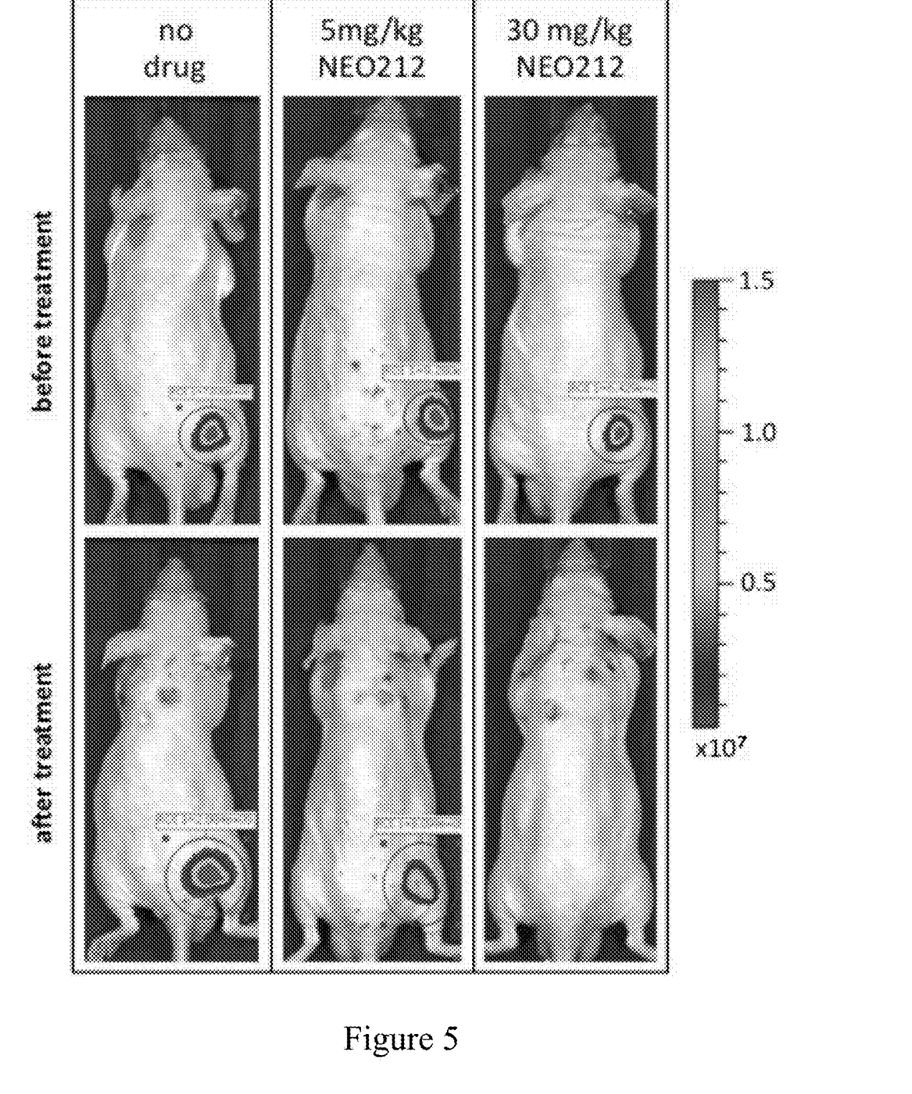
FIG. 5 shows whole-body bioluminescent imaging of NPC mice treated with vehicle and different dosages of TMZ-POH.

FIG. 5 shows the whole-body bioluminescent imaging of the animals from each of the three treatment groups, where top and bottom photo is from the same animal (the animal is selected from each of the treatment groups that represents the average response in that group). Top photos were taken before the onset of treatment. Bottom photos were taken one day after the 28-day treatment regimen. The heat (color) bar to the right shows the scale of light flux, where red represents stronger flux (more tumor growth) than blue (less tumor growth). As indicated by the colors of the target-shaped circle, which represents the tumor mass, there was increased tumor growth in the animal that did not receive drug treatment (left photos). Photos in the middle show one animal that received 5 mg/kg TMZ-POH, and in this animal the tumor became smaller (as indicated by the disappearance of the most intense red light flux). The animal to the right received 30 mg/kg TMZ-POH, and here light emission from the tumor became undetectable, indicating effective regression of the tumor mass—which was observed in half of the six animals in this treatment group (see FIG. 4).

EXAMPLE 3

In Vivo Studies of TMZ-POH in NPC Animal Models

In another experiment, TW4 NPC cells labeled with firefly luciferase gene were implanted into 12 athymic nude mice (Harlan Laboratories, Indianapolis, Ind.), which were separated into three groups of 4 animals each. All animals received once-daily injections for 28 days after onset of the tumor growth. The first group of animals was the control group which received daily injection of vehicle containing glycerol and ethanol but no active drug. In the second group, each animal received 5 mg/kg TMZ-POH once daily. In the third group, each animal received 30 mg/kg TMZ-POH once daily. The drug was administered by subcutaneous injection into the neck area.

Figure 6:
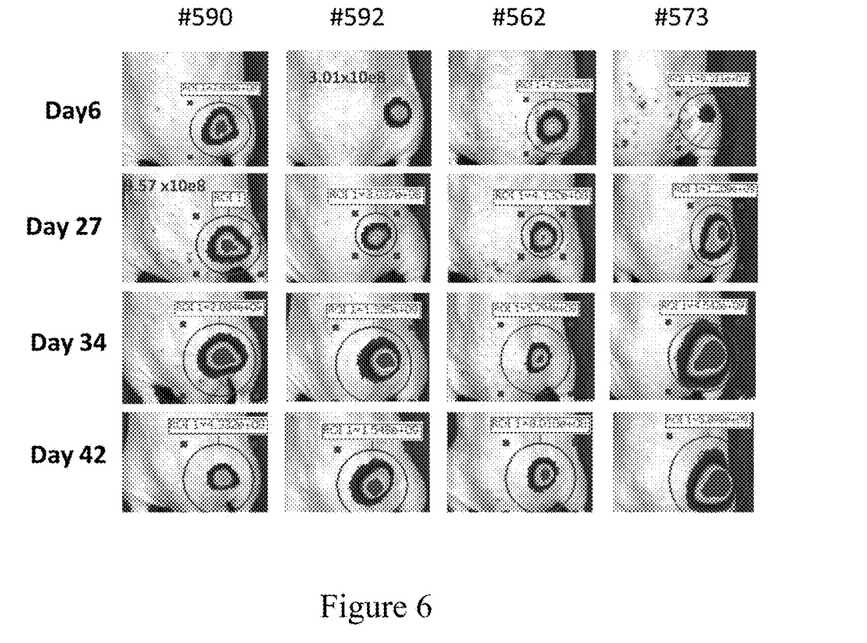
FIG. 6 shows bioluminescent imaging of 4 NPC mice treated with vehicle at different times during a testing period.

FIG. 6 shows bioluminescent imaging of 4 NPC mice that were treated with 30 μl/day of vehicle at selected days after treatment. As indicated by the colors of the target-shaped circle, which represents the tumor mass, there was increased tumor growth for each of the tested mice in this group during the course of the vehicle treatment, as well as during post-treatment.

Figure 7:
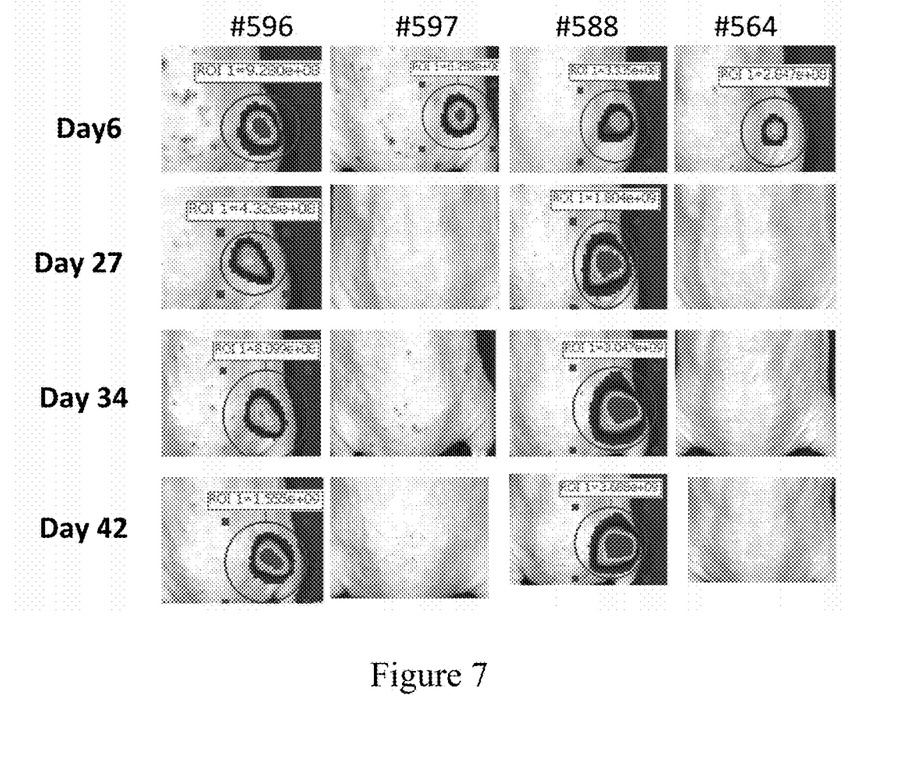
FIG. 7 shows bioluminescent imaging of 4 NPC mice treated with 5 mg/kg/day of TMZ-POH at different times during a testing period.

FIG. 7 shows bioluminescent imaging of 4 NPC mice that were treated with 5 mg/kg/day of TMZ-POH at selected days after treatment. In two mice (#597 and #564), the tumor was present in the test on day 6, but disappeared in the tests on day 27 and thereafter. In the other two mice (#596 and #588), the tumor persisted at each time of the tests until day 42.

Figure 8:
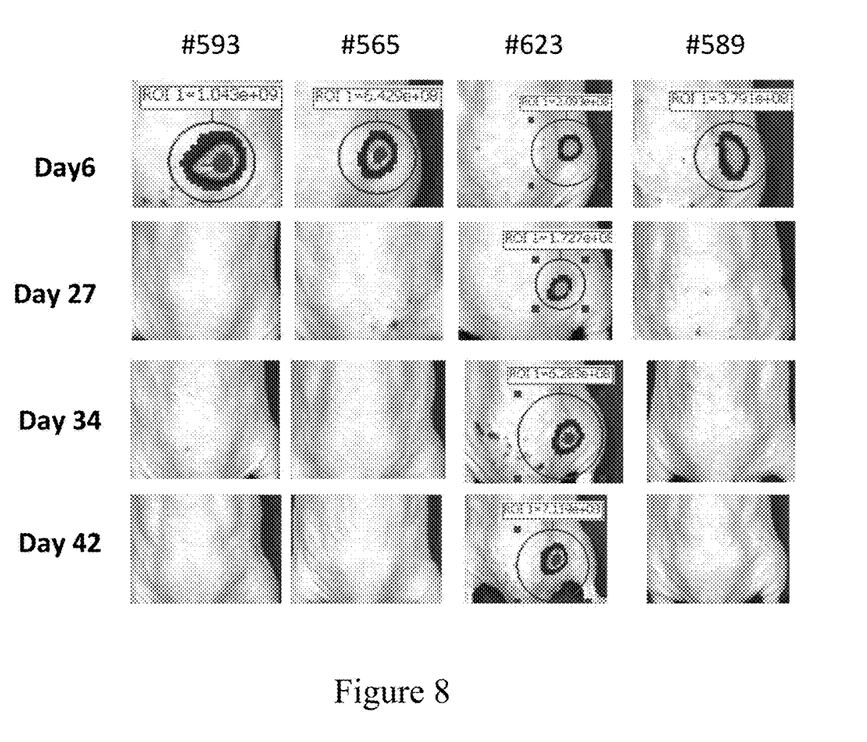
FIG. 8 shows bioluminescent imaging of 4 NPC mice treated with 30 mg/kg/day of TMZ-POH at different times during a testing period.

FIG. 8 shows bioluminescent imaging of 4 NPC mice that were treated with 30 mg/kg/day of TMZ-POH at selected days after treatment. In three of the mice (#593, #565, and #589), the tumor was present in the test on day 6, but disappeared in the tests on day 27 and thereafter. Only one mouse (#623) has persistent tumor during the testing period.

Figure 9:
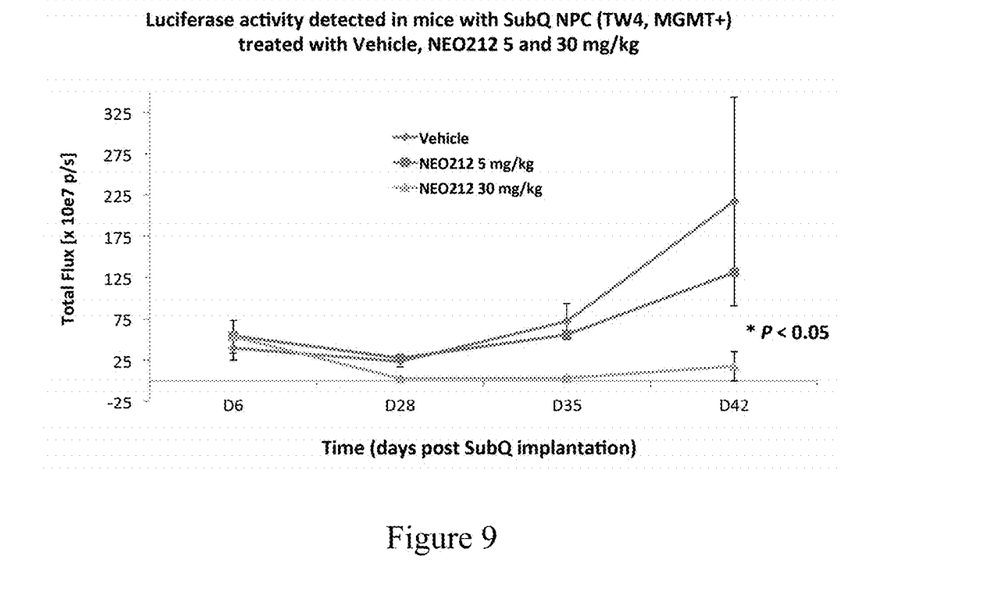
FIG. 9 shows time-course luciferase activity detected in each group of 12 NPC mice treated with vehicle and different dosages of TMZ-POH.

FIG. 9 shows time-course luciferase activity detected in each group of the 12 NPC mice during the testing period (Student Test *P<0.05). The results show that luciferase activity (which correlates to tumor size) decreased in mice treated with TMZ-POH compared with those in the control group, and that higher dose administration of TMZ-POH led to lower luciferase activity, demonstrating the effectiveness of TMZ-POH in the treatment of human nasopharyngeal carcinoma xenografts.

In summary, TMZ-POH revealed striking anticancer activity in preclinical nasopharyngeal carcinoma (NPC) models. In vitro, TMZ-POH exhibited substantially greater tumor cell killing potency than either of its individual components, POH or TMZ alone. In an in vivo mouse model, treatment with TMZ-POH resulted in clear therapeutic outcomes, in the absence of conspicuous side effects.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A method for treating oral cavity cancer in a mammal, the method comprising administering to the mammal a therapeutically effective amount of a perillyl alcohol carbamate, wherein the perillyl alcohol carbamate comprises perillyl alcohol conjugated with temozolomide (TMZ).

2. The method of claim 1, wherein the oral cavity cancer is pharyngeal cancer.

3. The method of claim 2, wherein the pharyngeal cancer is nasopharyngeal carcinoma.

4. The method of claim 1, further comprising treating the mammal with radiation.

5. The method of claim 1, further comprising administering to the mammal one or more chemotherapeutic agents.

6. The method of claim 5, wherein the chemotherapeutic agent is selected from the group consisting of Rituximab, Beuacizumab, Trastuzumab, Imaninib, Lenalidomide, Pemetrexed, Bortezomib, Cetuximab, Leuprorelin, Abiraterone, 5-Fluorouracil, Doxorubicin, Epirubicin, Gemeitabine, Methotrexate, all trans Retinoic Acid, Azacitidine, Azathioprine, Bleomycin, Carboplatin, Capecitabine, Cisplatin, Chlorambucil, Cyclophosphoramide, Cytarabine, Daunorubicin, Docetaxel, Doxifluridine, Epothilone, Etoposide, Hydroxyurea, Idarubicin, Irinotecan, Mechlorethamine, Mercaptopurine, Mitoxantrone, Oxaliplatin, Paclitaxel, Teniposide, Tioguanine, Topotecan, Valrubicin, Vincristine, Vinblastine, Vindesine, Vinorelbine and combinations thereof.

7. The method of claim 1, wherein the perillyl alcohol carbamate is administered by inhalation, orally, intravenously, subcutaneously or intramuscularly.

8. The method of claim 7, wherein the perillyl alcohol carbamate is administered intranasally using an atomizer.

9. The method of claim 1, wherein the perillyl alcohol carbamate is 3-methyl 4-oxo-3,4-dihydroimidazo[5,1-d][1,2,3,5]tetrazine-8-carbonyl)-carbamic acid-4-isopropenyl cyclohex-1-enylmethyl ester.

10. The method of claim 1, wherein the perillyl alcohol carbamate is administered by a nasal delivery device.

11. The method of claim 10, wherein the nasal delivery device is selected from the group consisting of an intranasal inhaler, an intranasal spray device, an atomizer, a nebulizer, a metered dose inhaler (MDI), a pressurized dose inhaler, an insufflator, a unit dose container, a pump, a dropper, a nasal spray bottle, a squeeze bottle and a bi-directional device.

* * * * *